(12) United States Patent
Gorochow (10) Patent No.: US 10,076,428 B2
(45) Date of Patent: Sep. 18, 2018

(54) EXPANSION RING FOR A BRAIDED STENT (71) Applicant: DePuy Synthes Products, Inc., Raynham, MA (US)

(72) Inventor: Lacey Gorochow, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/246,784

(22) Filed: Aug. 25, 2016

(65) Prior Publication Data
US 2018/0055665 A1 Mar. 1, 2018

(51) Int. Cl.
*A61F 2/90* (2013.01)
*A61F 2/844* (2013.01)
*A61F 2/88* (2006.01)
*A61F 2/91* (2013.01)
*A61F 2/852* (2013.01)
*A61F 2/86* (2013.01)

(52) U.S. Cl.
CPC .............. *A61F 2/844* (2013.01); *A61F 2/852* (2013.01); *A61F 2/86* (2013.01); *A61F 2/885* (2013.01); *A61F 2/90* (2013.01); *A61F 2/91* (2013.01); *A61F 2210/0014* (2013.01); *A61F 2220/005* (2013.01); *A61F 2220/0058* (2013.01); *A61F 2230/0013* (2013.01); *A61F 2230/0054* (2013.01); *A61F 2310/00023* (2013.01)

(58) Field of Classification Search
CPC ...... A61F 2/07; A61F 2/82; A61F 2/88; A61F 2/91
USPC ............................................... 623/1.11–1.53
See application file for complete search history.

(56) References Cited

U.S. PATENT DOCUMENTS

| 5,522,881 | A | 6/1996 | Lentz |
| 5,556,413 | A | 9/1996 | Lam |
| 5,725,549 | A | 3/1998 | Lam |
| 5,755,772 | A | 5/1998 | Evans et al. |
| 6,036,725 | A | 3/2000 | Avellanet |
| 6,099,559 | A | 8/2000 | Nolting |
| 6,123,722 | A | * 9/2000 | Fogarty ............. A61F 2/07 623/1.1 |
| 6,168,621 | B1 | 1/2001 | Vrba |
| 6,319,278 | B1 | 11/2001 | Quinn |
| 6,409,755 | B1 | 6/2002 | Vrba |
| 6,699,277 | B1 | 3/2004 | Freidberg et al. |
| 6,740,113 | B2 | 5/2004 | Vrba |

(Continued)

FOREIGN PATENT DOCUMENTS

| EP | 2777638 A1 | 9/2014 |
| WO | 2001015632 A1 | 3/2001 |
| WO | 2005087138 A1 | 9/2005 |

OTHER PUBLICATIONS

Extended European Search Report dated Feb. 16, 2018 during the prosecution of European Patent Application EP17187782.

*Primary Examiner* — Suzette J Gherbi
(74) *Attorney, Agent, or Firm* — Troutman Sanders LLP (57) ABSTRACT

A braided stent system includes an expansion ring attached to internal and external surfaces of a lumen. A frame of the ring may impart an outwardly expanding radial force to the lumen, the frame including a plurality of elongate members joined at a coupling and at first and second intersections opposite the coupling. A clip can extend from the intersections and can be operable to slidably secure the frame to the inner and outer surfaces of the lumen.

17 Claims, 5 Drawing Sheets

(56) References Cited

U.S. PATENT DOCUMENTS

| | | | |
|---|---|---|---|
| 6,770,089 B1 | 8/2004 | Hong et al. | |
| 6,911,040 B2 | 6/2005 | Johnson et al. | |
| 6,945,994 B2 | 9/2005 | Austin et al. | |
| 7,122,052 B2 | 10/2006 | Greenhalgh | |
| 7,288,111 B1 | 10/2007 | Holloway et al. | |
| 7,628,806 B2 | 12/2009 | Yampolsky et al. | |
| 7,632,302 B2 | 12/2009 | Vreeman et al. | |
| 7,655,034 B2 | 2/2010 | Mitchell et al. | |
| 7,708,773 B2 | 5/2010 | Pinchuk et al. | |
| 7,758,629 B2 | 7/2010 | Holloway et al. | |
| 7,806,919 B2 | 10/2010 | Bloom et al. | |
| 7,806,923 B2 | 10/2010 | Moloney | |
| 7,998,187 B2 | 8/2011 | Hartley et al. | |
| 8,043,357 B2 | 10/2011 | Hartley | |
| 8,357,194 B2 | 1/2013 | Majercak | |
| 8,372,133 B2* | 2/2013 | Douk | A61F 2/90 623/1.12 |
| 8,449,600 B2 | 5/2013 | Hartley et al. | |
| 8,562,666 B2 | 10/2013 | Bonsignore | |
| 8,672,992 B2 | 3/2014 | Orr | |
| 8,709,065 B2 | 4/2014 | Chobotov | |
| 8,734,501 B2 | 5/2014 | Hartley et al. | |
| 9,339,260 B2* | 5/2016 | Eidenschink | A61B 17/0057 |
| 2003/0009211 A1* | 1/2003 | DiCarlo | A61F 2/07 623/1.13 |
| 2006/0212113 A1* | 9/2006 | Shaolian | A61F 2/07 623/1.35 |
| 2007/0191922 A1 | 8/2007 | Hartley | |
| 2008/0009934 A1* | 1/2008 | Schneider | A61F 2/95 623/1.11 |
| 2009/0234429 A1 | 9/2009 | Lau | |
| 2011/0004237 A1* | 1/2011 | Schneider | A61F 2/86 606/194 |
| 2011/0264186 A1 | 10/2011 | Berglung et al. | |
| 2012/0035714 A1 | 2/2012 | Ducke et al. | |
| 2016/0030155 A1* | 2/2016 | Cox | A61F 2/07 623/1.13 |
| 2016/0235561 A1* | 8/2016 | Wrobel | A61F 2/848 |
| 2017/0079813 A1* | 3/2017 | Bar | A61F 2/07 |

* cited by examiner

- 110 Assembling expansion rings with a lumen of the braided stent body

- 120 Selectively attaching each expansion ring with inner and outer surfaces of the lumen of the braided stent body, each expansion ring imparting an outwardly expanding radial force to the braided stent body thereby maintaining the lumen of the braided stent body in an opened position

- 130 Slidably attaching a plurality of outer strut members of the clip to the inner surface of the lumen, each outer strut member being aligned and extended from the first intersection and joined at an end opposite the first intersection

- 140 Slidably attaching a plurality of center strut members of the clip to the outer surface of the lumen, each center strut member being disposed in a gap formed between the outer strut members, the center strut members being aligned and extended from the second intersection

EXPANSION RING FOR A BRAIDED STENT

FIELD

The present disclosure relates generally to treatment of certain defects in a vasculature of a patient and more particularly, to expanding braided stents to a treatment site in a vasculature of a patient.

BACKGROUND

Stents are understood as tubular reinforcements that can be inserted into a blood vessel to provide an open path within the blood vessel. Stents have been widely used in intravascular angioplasty treatment of occluded cardiac arteries, wherein the stent may be inserted after an angioplasty procedure to prevent restenosis of the artery. Stents are often deployed by use of delivery devices which cause the stent to open with the objective of reinforcing the artery wall and provide a clear through-path in the artery thereby preventing restenosis.

However, the weakness and non-linear nature of the neurovasculature limits the applicability of such stents in procedures, for example, in repairing neurovascular defects. Furthermore, known delivery methods are less useful in vasoocclusive surgery, particularly when tiny vessels, such as those found in the brain, are to be treated. Accordingly, a need exists for a stent that can be used with delivery techniques in vasoocclusive treatment of neurovascular defects that provides selective reinforcement in the vicinity of the neurovascular defect. A need also exists for a stent that reduces trauma or risk of rupture to the blood vessel. It is with respect to these and other considerations that the various embodiments described below are presented.

SUMMARY

In some aspects, the present disclosure relates to a braided stent system for delivery into a blood vessel is disclosed. They system may include a stent body having a lumen formed by a plurality of braided members with interstices formed therebetween. An expansion ring may be mechanically connected to inner and outer surfaces of the lumen of the stent body and be operable to open the expansion ring and anchor the stent body for receiving a flow diverter. The frame may include a shape memory configuration with a diameter larger than available expansion of the stent body.

In an example embodiment, the frame may be operable to impart an outwardly expanding radial force to the stent body. The frame may include a plurality of elongate members joined at a coupling and at first and second intersections opposite the coupling. At least one clip may extend from the intersections and may be operable to slidably secure the frame to the inner and outer surfaces of the lumen. The clip can include a plurality of outer strut members that are aligned and extended from the first intersection and joined at an end opposite the first intersection. The outer strut members may also be slidable along the inner surface of the lumen. A plurality of center strut members can be disposed in a gap formed between the outer strut members and also be aligned and extend from the second intersection. The center strut members may be slidable along the outer surface of the lumen and can be attached at an end opposite the second intersection in a pore in communication with the outer strut members.

In an example embodiment, the center strut members can be spaced a predetermined distance from the outer strut members. A laser-cut clipping pattern can be formed between the outer and center strut members. The center and outer strut members can also be attached at the pore by being welded, soldered, or glued together. However, the clip is not so limited and instead the center strut members can be slidable along the outer surface of the lumen and operable to bias towards the lumen (e.g. inwardly) by a resistance element defined between the center strut members and the second intersection. The resistance element could be a spring, bias or bowed configuration of the center strut members and/or the outer strut members to bias towards the lumen to secure the clip with the lumen as desired. Optionally, the plurality of elongate members of the frame may be bowed causing the frame to be resistant to compression. The elongate members may also be twistable a predetermined amount about the coupling. At least one pair of the plurality of elongate members can be formed in a V-shape, a U-shape, or an elliptical curve.

In other embodiments, the shape memory configuration of the expansion ring may include a metal alloy tubing structure such as nickel titanium that is laser-cut.

In other example embodiments, the stent body may include a proximal end, a distal end, and a central portion disposed therebetween. The first expansion ring can be disposed on or adjacent the distal or proximal end of the stent body with the coupling of the plurality of elongate members being joined at or adjacent the respective distal or proximal end. A second expansion ring can also be included that is mechanically connected to inner and outer surfaces of the lumen of the stent body. The second expansion ring can have a frame with a shame memory configuration with a diameter larger than available expansion of the stent body and the second expansion ring may be operable to open and anchor the stent body for receiving a flow diverter. The frame of the second expansion ring can similarly include a plurality of elongate members joined at a coupling and at first and second intersections opposite the coupling. At least one clip can be included in the second expansion ring that extends from the intersections and may be operable to slidably secure the frame to the inner and outer surfaces of the lumen.

A method of deploying a braided stent body into a vessel is also contemplated. The method includes assembling a plurality of expansion rings with a lumen of the braided stent body, the lumen of the braided stent body being formed by a plurality of braided members with interstices formed therebetween and selectively attaching each expansion ring with inner and outer surfaces of the lumen of the braided stent body, each expansion ring imparting an outwardly expanding radial force to the braided stent body thereby maintaining the lumen of the braided stent body in an opened position. Each expansion ring can have a plurality of elongate members joined at a coupling and first and second intersections opposite the coupling; and at least one clip extended from the intersections and operable to secure the frame to the inner and outer surfaces of the lumen; slidably attaching a plurality of outer strut members of the clip to the inner surface of the lumen, each outer strut member being aligned and extended from the first intersection and joined at an end opposite the first intersection; and slidably attaching a plurality of center strut members of the clip to the outer surface of the lumen, each center strut member being disposed in a gap formed between the outer strut members, the center strut members being aligned and extended from the second intersection.

The method may also include attaching the center and outer strut members together at an end opposite the second and first intersections in a pore in communication of the strut members; forming the shape memory configuration of each expansion ring with a metal alloy tubing structure; biasing the center and outer strut members together by incorporating a bias element on or about the first and second intersections of the clip; spacing the outer and center strut members a predetermined distance; and/or forming an outer access point at a pore between the outer and center strut members.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braided stent body to the vasculature of a subject.

It is to be understood that a "self-expanding" stent is a stent wherein the particular stent fully deploys upon emerging through a delivery device such as a sheath, microcatheter, or the like. In this respect, when a self-expanding braided stent emerges, unrestrained outside of the respective delivery device, it should expand and be deployed in the vasculature. However, due to radial forces and friction, braided stent deployment and recapture following deployment is difficult.

Braided stents may be formed from a plurality of elongate members (e.g. metal wires, polymeric fibers, or strands of material) and these members can be very useful in treatment of neurovascular defects. However, when such braided members are intended to be self-expanding in a lumen of a stent body, known manners of activation of the initially expanding end struggle to adequately, reliably, and fully open so that the initially expanding end can be used as an anchor point. Moreover, braided stents have been known to exhibit high internal friction that resists the inherent radial expansion force of the self-expanding braided stent when being deployed to an opened state. Specifically, the relatively high internal friction can render it difficult to open the initially expanding end of the stent which results in deficiencies in anchoring and deployment. This is particularly true for braided stents delivered to the desired vessel location through use of a delivery sheath, microcatheter, or the like, since in a closed state (e.g. compressed or crimped) the stent body typically exhibits friction between the braided members and the delivery sheath or microcatheter.

In practice, braided stents can be delivered to a particular vessel by advancing a blunt surface against a proximal end of the braided stent causing the braided stent to axially compress and expand radially. This expansion within the delivery sheath or microcatheter can result in an increased normal force being applied to the inner surface of the delivery sheath, microcatheter, or the like thereby also increasing friction caused by the braided stent.

Expansion rings have been used with braided stents to resolve these and other problem. However, given the size and application, rings that are formed from memory structures (e.g. metal alloy) can be difficult to manufacture. This is because the respective ring must be placed within the inner lumen of the braid so the ring can aid in outwardly expanding the braid. Attaching the expansion ring inside the braid can be difficult due to the limited access to an attachment zone between the braid and the expansion ring. Specifically, it can be more difficult for an operator to access the expansion ring from the inner lumen of the braid than from outside of the braided stent. Such rings may also provide an inner surface with which the bumps on the delivery wire of the braided stent can engage.

Known solutions to these issues have depended on factors such as material, size, cell design, internal friction, and extra manipulation by the end-user to reliably, quickly and adequately open the braided stents. In turn, success of the braided stent relied heavily on end-user accuracy in delivery which unnecessarily increases risk of injury to the patient. Moreover, such braided, self-expanding stents can be difficult to recapture after being delivered and/or deployed.

One attempt at resolving these problems has included looping a tiny wire through the braided stent and the expansion ring of metal alloy and then tying the two components together. This method is not ideal, however, because the tiny wire must be added to the system. If this wire were to break off of the implant in the patient, it could also result in an emboli complication.

The herein disclosed expansion ring 1 resolves these and other problems of the art when assembled with a braided stent body 12 and forming assembly 10. In an example embodiment, assembly 10 permits the operator to place ring 1 that is constructed with a shape memory structure (e.g. a metal alloy such as nickel titanium [NiTi] (also known as nitinol) within an inner lumen 20 of body 12, while still having an attachment zone of ring 1 be disposed outside of body 12. Ring 1 may be designed to facilitate opening and anchoring of body 12 to help the operator accurately and easily place a flow diverter. Preferably, ring 1 may be laser cut with a shape memory configuration (e.g. a metal alloy tubing such as nitinol) that has a diameter that is larger than the available expansion of the braided stent body.

Figure 1:
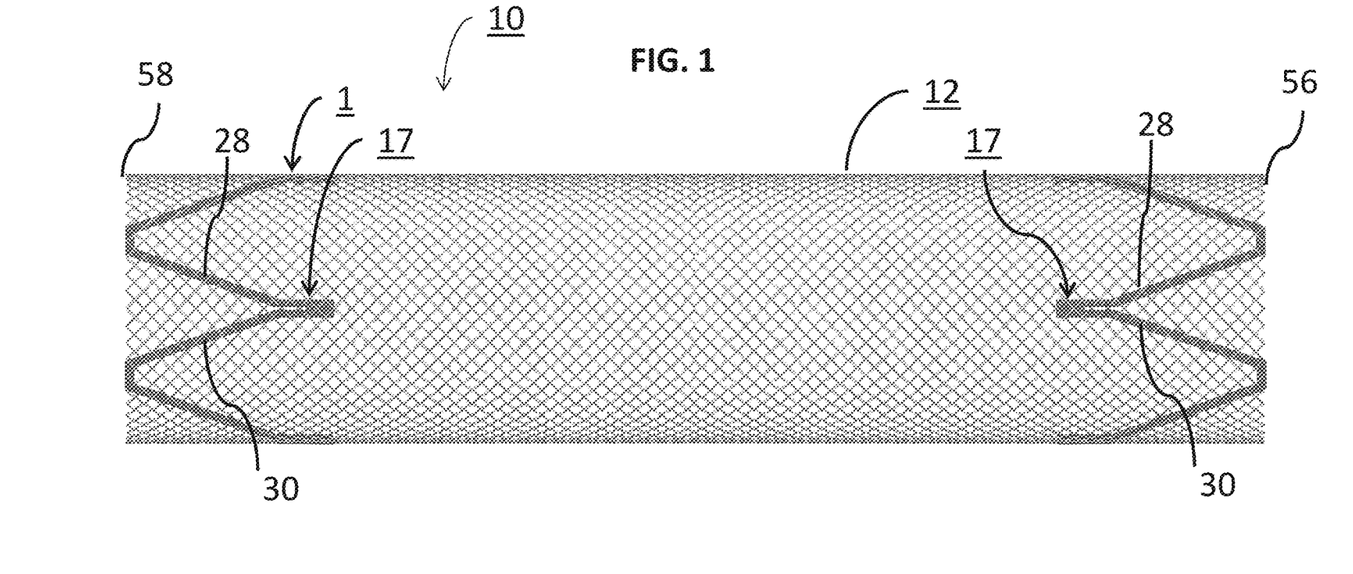
FIG. 1 depicts a side plan view of one embodiment of the two of the disclosed expansion rings assembled at first and second ends of a tubular braided stent body.
Figure 2:
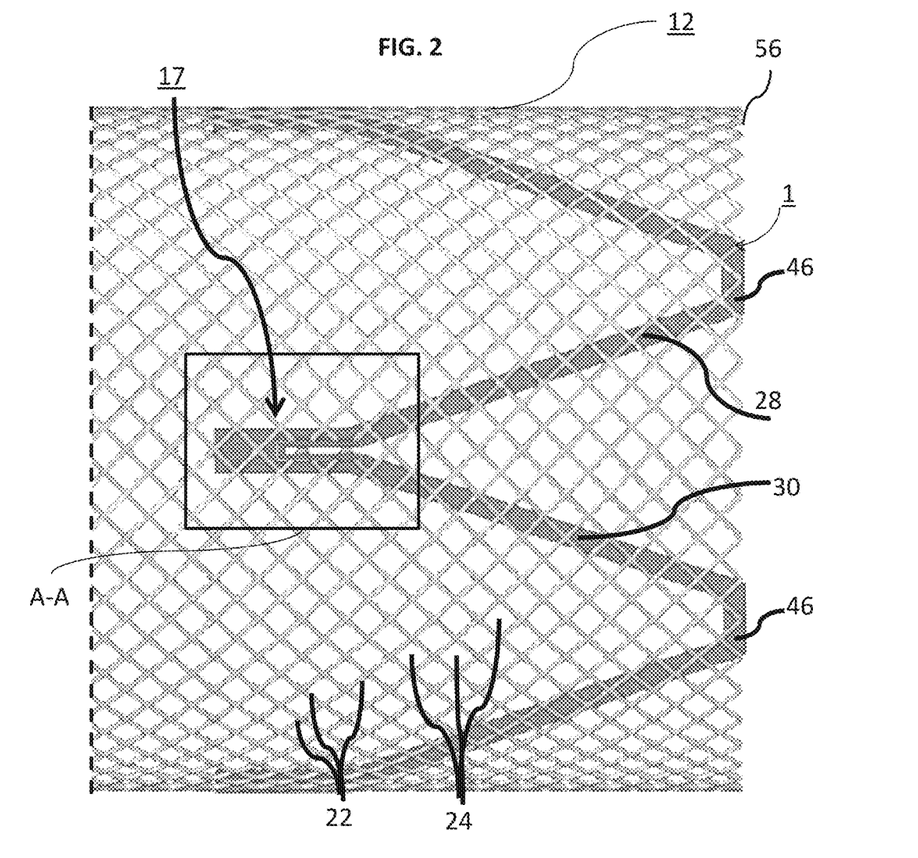
FIG. 2 depicts a close-up side plan view of one of the rings of FIG. 1 assembled at a first end of the tubular braided stent body.

In the following description, references are made to the accompanying drawings that form a part hereof and that show, by way of illustration, specific embodiments or examples. In referring to the drawings, like numerals represent like elements throughout the several figures. Turning to FIGS. 1 and 2, side plan views of the herein disclosed ring 1 and corresponding body 12 are shown. Body 12 of FIGS. 1 and 2 may be formed from a plurality of elongate members 22 braided or otherwise arranged to form a plurality of interstices 24. Members 22 may be formed from two or more metal wires, or polymeric fibers or strands of material. Ring 1 may be constructed from one or multiple elongate members 28 and 30 interconnected at first 46 and second 36 intersections that together form a frame of ring 1 capable of imparting one or more additive radial forces to an inner wall and/or an outer wall of lumen 20 of body 12. Assembling one or more multiple rings 1 with body 12 as shown results in a relatively easy delivery of body 12 within the vasculature that is reliable with reduced risk of injury for the end-user.

In this regard, ring 1 may be selectively positioned and arranged for rapid opening and/or maintaining body 12 in an opened position without having to weld, solder, glue, or otherwise connect ring 1 to body 12 itself. Ring 1 can be assembled at a first end 58 of body 12 and ring 1 can also be assembled a second, opposite end 56 of body 12. It is to be understood that any number of rings 1 can be assembled with body 12 including at only one of ends 56 and 58 as well as at any number of locations between ends 56 and 58 of body 12.

Figure 3:
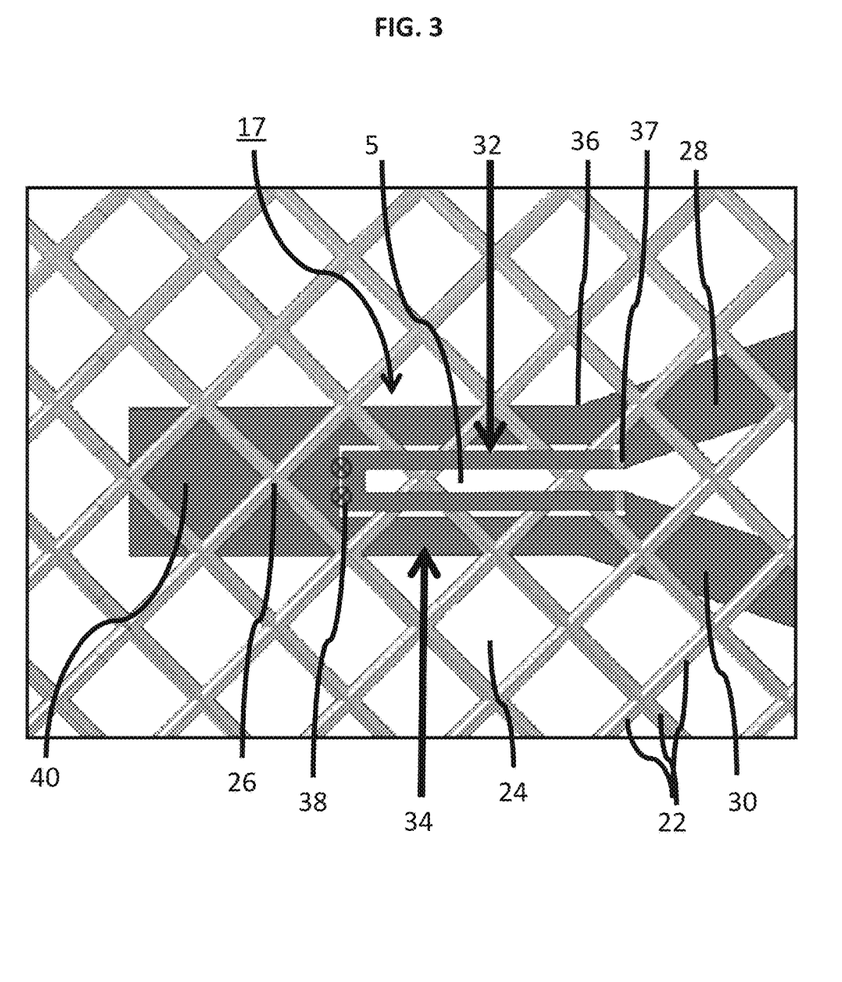
FIG. 3 is a close-up view of plane A-A of FIG. 2 showing certain features of the expansion ring assembled with the tubular braided stent body.

FIG. 2 is a close-up of an exemplary ring 1 of FIG. 1 assembled at end 56. As can be seen, assembling ring 1 with body 12 increases an outwardly extending radial expansion force at end 56 of body 12, opposing end 58, and/or a central portion defined between each end 56 and 58. Ring 1 can include one or a plurality support clips 17 interconnected with first and second elongate members 28 and 30 that collectively cause the ring 1 to fully anchor itself with the lumen 20 of body 12. Clip 17 mechanically secures each ring with body 12 by being interlaced with the braided, elongate members 22 of body 12 as discussed more particularly below. Turning to FIG. 3 is a close up view of plane A-A of FIG. 2 more clearly showing clip 17 interlaced with the interstices 24 and braided, elongate members 22. Preferably, clip 17 of ring 1 may be a "paper clip" type ring with a clip pattern that is formed by a center strut member 32 and an outer strut member 34 into one end of a metal alloy tube.

As can be previously seen in FIGS. 1-2, first elongate member 28 can be joined with second elongate member 30 at a second intersection 46. Second intersection 46 may also be attached to body 12 at respective ends 56, 58, any portion of body 12 therebetween, or may be oriented to bias into or urged against inner lumen 20 of body 12. As can be seen in FIG. 3, each member 28 and 30 is connected to or in communication with clip 17 at intersections 36 and 37, opposite intersection 46. Specifically, strut member 34 extends from members 28 or 30 at respective intersection 36 while strut member 32 extends from members 28 or 30 at respective intersection 37. As can be seen, clip 17 may include two aligned members 34 that are elongate and extended away from respective first intersection 36 respective end 56 or 58 towards and joined at connector end 40. Clip 17 may also include two members 32 that are aligned with each other and relatively smaller in length and/or thickness than members 34, each member 32 being disposed internal to a gap formed by members 34 and aligned with members 34. A gap may also be formed between each member 32 through which one or more braided pairs 26 of wires 22 can pass. Each member 32 may also be elongate and extend away from respective intersection 37 towards and joined at connector end 40 through one or more welds, soldered connections, chemical adhesive or the like with the one or more pores 38.

The clip pattern of members 32 and 34 may be laser cut into the metal alloy tube of ring 1. However, ring 1 is not so limited and the clip pattern of members 32 and 34 may be formed into one end of the metal alloy tube by any other manufacturing technique as needed or required including 3-d printing, a CNC machine, a lather, additive manufacturing, etc. Members 32 and 34 together allow the operator to slide ring 1 through one or more interstices 24 of the braided stent body 12 in a manner similar to sliding a paper-clip over a piece of paper. In this respect, members 32 may slidably inserted over and/or external to wires 22 of body 12 whereas members 34 may slidably inserted inside of wires 22 of body 12. Members 32 and 34 may then be welded, soldered, glued, or otherwise connected together inside one or more pores 38, or open space of body 12 to secure ring 1 to body 12. For example, FIGS. 2-3 depict the herein discussed body 12 assembled with ring 1 at a first end 56 in an example embodiment. Member 34 also provides a solid, stable surface operable to aid in the delivery of system 10 when crimped down into body 12 such as a microcatheter. Alternatively, members 32 and 34 may be biased or otherwise operable to be urged against each other with a resistance element of intersection 37 (e.g. a spring or bowed configuration) so that members 32 and 34 naturally pivot towards each other. In this embodiment, members 32 and 34 may or may not be connected at pore 38. Member 32 may be heat treated so that it can be raised a predetermined distance above the outer strut member 34. In this respect, the raised member 32 may allow the operator to more easily place members 32 and 34 through interstices 24 during assembly as there would be more separation between the clip and the braided stent wires.

As can be seen, while members 28 and 30 are seen integrally formed with each other in FIGS. 1-4 at intersections 36, 37, and 46, ring 1 is not so limited and members 28 and 30 may be removably attached to each other through a fastener including a band, bolt, clamp, coupling, dowel, hook, latch, key, or the like. Members 28 and 30 may also be adhered to each other or welded to form one or more of intersections 36, 37, and 46. Additionally, if one or more fasteners is used in a particular implementation, the fastener can be removably connected or welded, soldered, and/or crimped thereon. Fasteners and/or members 28 and 30 can be formed of a radiopaque metal, such as platinum or tantalum, or may be formed of a non-radiopaque material, such as stainless steel.

By adding clip 17 to ring 1, each ring 1 is allowed to interlace with body 12 and operatively attach to both the inner and outer portions of body 12 without a permanent or rigid attachment to body 12 itself by welding, soldering or through a chemical adhesive. Once members 32 and 34 are effectively assembled with body 12, braided members 22 can also move independently from ring 1 which removes the adverse impact that a permanent or rigid attachment could otherwise have on body 12 to expand when assembled with an expansion ring. Intersection 46 may also include a rotatable and/or twistable coupling so that ring 1 is capable of flexing a predetermined amount when body 12 and ring 1 is in use.

Figure 4:
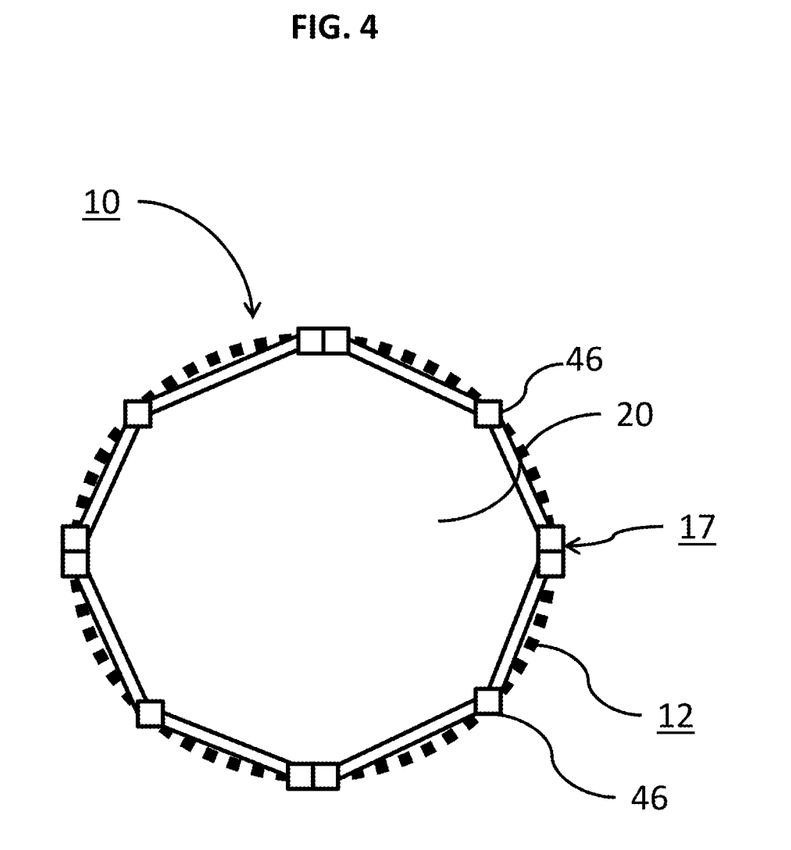
FIG. 4 is forward plan view of an exemplary expansion ring when assembled with a tubular braided stent body showing its inner lumen.

FIG. 4 is a forward plan view of an exemplary ring 1 when assembled with body 12 showing each of clips 17 and corresponding intersections 46 with regards to lumen 20 of body 12 in the uncompressed state. The herein disclosed ring 1 could be used with any number of clips 17 as needed or required depending on need or preference. It is to be understood that ring 1 can be a compression element capable of flexing a predetermined amount. In this respect, ring 1 could move between a compressed configuration before deployment within the vasculature as well as a deployed configuration with a lumen 20 having a greater diameter than the compressed configuration. Elongate members 28 and/or 30 may also include a curved or arched portion that bows with a predetermined resistance to compression. It is to be understood that each pair of members 28 and 30 in ring 1 may have the same or a different resistance so that ring 1 can be individualized for the specific vasculature implementation. Additionally, members 28 and 30 ring 1 may be formed as a V-shape as shown in FIGS. 1-3 with acute and/or oblique angles. However, ring 1 is not so limited and instead of being V-shaped, members 28 and 30 can be formed as "U" shaped, elliptical shaped, generally curved, loop or bight at the junction portion.

The herein disclosed ring 1 and corresponding system aids in manufacturing an easy and safe to use braided stent by utilizing an outer access point formed at pore 38 between members 32 and 34 as well as utilizing a connection along the inner surface of body 12 via members 34 and corresponding members 28 and 30.

Ring 1 and its constituent features may be formed of a superelastic material, such as Nitinol, or may be formed of a non-superelastic material, such as spring steel or MP35N, an alloy of 35% nickel, 35% cobalt, 20% chromium, and 10% molybdenum, by weight. Members 28 and 30 of each ring 1 may also be formed from a shape memory material having a shape memory position in the opened state.

Figure 5:
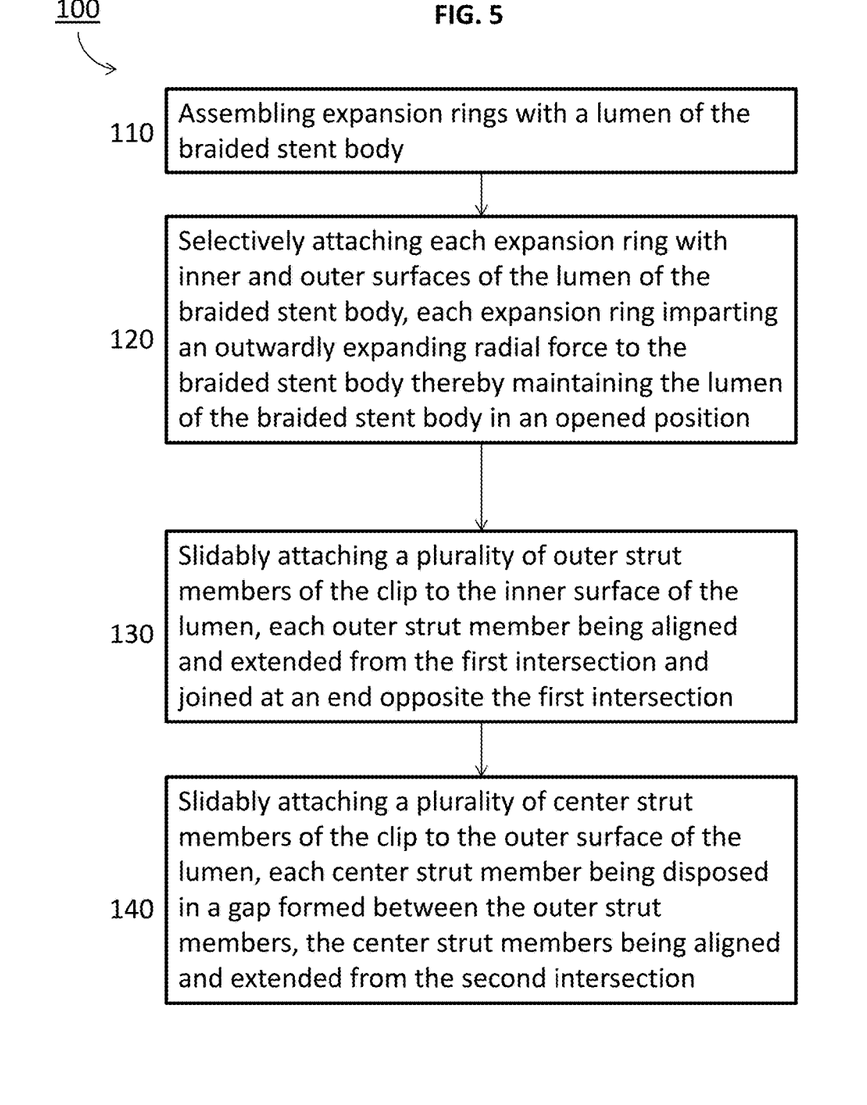
FIG. 5 is a schematic overview of one example method of deploying an exemplary braided stent body into a vessel.

Turning to FIG. 5, a method 100 of deploying one or more of any of the herein disclosed rings 1 with lumen 20 of body 20. The method 100 can include steps 110 through 140. Step 110 may include assembling one or more rings 1 with lumen 20 of body 20. Step 120 may include selectively attaching each ring 1 with inner and outer surfaces of lumen 20 so that each ring 1 may impart an outwardly expanding radial force to body 12 thereby maintaining lumen 20 in an opened position. Step 130 may include slidably attaching outer members 34 of clip 17 to the inner surface of lumen 20, each outer strut member 34 being aligned and extended from the first intersection 36 and joined at an end opposite the first intersection (e.g. pore(s) 38). Step 140 may include slidably members 32 of clip 17 to the outer surface of lumen 20, each member 32 being disposed in gap 5 formed between members 34, members 32 being aligned and extended from the second intersection 37.

Others steps may be included in method 100 such as attaching members 32 and 34 together at an end opposite intersections 36,37 in one or more pores 38, crimping the members 34 into the outer surface of lumen 20, forming the shape memory configuration of each ring 1 with a metal alloy tubing structure, biasing members 32, 34 together by incorporating a bias element on or about intersections 36, 37 of clip 17, spacing members 32, 34 a predetermined distance apart, and/or forming an outer access point at one or more pores 38 between members 32, 34.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A braided stent system comprising:
 a stent body having a lumen formed by a plurality of braided members with interstices formed therebetween;
 an expansion ring mechanically connected to inner and outer surfaces of the lumen of the stent body, the expansion ring having a frame with a shape memory configuration with a diameter larger than available expansion of the stent body,
 the frame imparting an outwardly expanding radial force to the stent body, the frame comprising a plurality of elongate members joined at a coupling and at first and second intersections opposite the coupling; and
 at least one clip extended from the intersections and operable to slidably secure the frame to the inner and outer surfaces of the lumen;
 wherein the expansion ring is operable to open and anchor the stent body for receiving a flow diverter, wherein the clip comprises:
 a plurality of outer strut members aligned and extended from the first intersection and joined at an end opposite the first intersection, the outer strut members being slidable along the inner surface of the lumen; and a plurality of center strut members disposed in a gap formed between the outer strut members, the center strut members being aligned and extended from the second intersection;

wherein the center strut members are slidable along the outer surface of the lumen and attached at an end opposite the second intersection in a pore in communication with the outer strut members.

2. The system of claim 1, wherein a laser-cut clipping pattern is formed between the outer and center strut members.

3. The system of claim 1, wherein the center strut members are spaced a predetermined distance from the outer strut members.

4. The system of claim 1, wherein the center and outer strut members are attached at the pore by being welded, soldered, or glued.

5. The system of claim 1, wherein the shape memory configuration of the expansion ring comprise a metal alloy tubing structure.

6. The system of claim 1, wherein the metal alloy is nickel titanium and the structure is laser-cut.

7. The system of claim 1, wherein the shape memory configuration is formed from a shape memory material having a shape memory position in an opened state.

8. The system of claim 1, wherein the plurality of elongate members of the frame are bowed causing the frame to be resistant to compression, the elongate members being twistable a predetermined amount about the coupling.

9. The system of claim 1, wherein the stent body includes a proximal end, a distal end, and a central portion disposed therebetween; and wherein the first expansion ring is disposed on or adjacent the distal or proximal end of the stent body with the coupling of the plurality of elongate members being joined at or adjacent the respective distal or proximal end.

10. A braided stent system comprising:
a stent body having a lumen formed by a plurality of braided members with interstices formed therebetween;
an expansion ring mechanically connected to inner and outer surfaces of the lumen of the stent body, the expansion ring having a frame with a shape memory configuration with a diameter larger than available expansion of the stent body,
the frame imparting an outwardly expanding radial force to the stent body, the frame comprising a plurality of elongate members joined at a coupling and at first and second intersections opposite the coupling; and
at least one clip extended from the intersections and operable to slidably secure the frame to the inner and outer surfaces of the lumen;
wherein the expansion ring is operable to open and anchor the stent body for receiving a flow diverter, wherein the clip comprises:
a plurality of outer strut members aligned and extended from the first intersection and joined at an end opposite the first intersection; and
a plurality of center strut members disposed in a gap formed between the outer strut members, the center strut members being aligned and extended from the second intersection;
wherein the center strut members are slidable along the outer surface of the lumen and operable to bias inward by a resistance element defined between the center strut members and the second intersection.

11. A braided stent system comprising:
a stent body having a lumen formed by a plurality of braided members with interstices formed therebetween;
an expansion ring mechanically connected to inner and outer surfaces of the lumen of the stent body, the expansion ring having a frame with a shape memory configuration with a diameter larger than available expansion of the stent body,
the frame imparting an outwardly expanding radial force to the stent body, the frame comprising a plurality of elongate members joined at a coupling and at first and second intersections opposite the coupling; and
at least one clip extended from the intersections and operable to slidably secure the frame to the inner and outer surfaces of the lumen;
wherein the expansion ring is operable to open and anchor the stent body for receiving a flow diverter;
wherein the plurality of elongate members of the frame are bowed causing the frame to be resistant to compression, the elongate members being twistable a predetermined amount about the coupling;
wherein at least one pair of the plurality of elongate members is formed in a V-shape, a U-shape, or an elliptical curve.

12. A braided stent system comprising:
a stent body having a lumen formed by a plurality of braided members with interstices formed therebetween;
an expansion ring mechanically connected to inner and outer surfaces of the lumen of the stent body, the expansion ring having a frame with a shape memory configuration with a diameter larger than available expansion of the stent body,
the frame imparting an outwardly expanding radial force to the stent body, the frame comprising a plurality of elongate members joined at a coupling and at first and second intersections opposite the coupling; and
at least one clip extended from the intersections and operable to slidably secure the frame to the inner and outer surfaces of the lumen;
wherein the expansion ring is operable to open and anchor the stent body for receiving a flow diverter;
wherein the stent body includes a proximal end, a distal end, and a central portion disposed therebetween;
wherein the first expansion ring is disposed on or adjacent the distal or proximal end of the stent body with the coupling of the plurality of elongate members being joined at or adjacent the respective distal or proximal end;
a second expansion ring mechanically connected to inner and outer surfaces of the lumen of the stent body, the second expansion ring having a frame with a shape memory configuration with a diameter larger than available expansion of the stent body, wherein the second expansion ring is operable to open and anchor the stent body for receiving a flow diverter;
the frame comprising a plurality of elongate members joined at a coupling and at first and second intersections opposite the coupling; and at least one clip extended from the intersections and operable to slidably secure the frame to the inner and outer surfaces of the lumen.

13. A method of deploying a braided stent body into a vessel, the method comprising:
assembling a plurality of expansion rings with a lumen of the braided stent body, the lumen of the braided stent body being formed by a plurality of braided members with interstices formed therebetween;
selectively attaching each expansion ring with inner and outer surfaces of the lumen of the braided stent body, each expansion ring imparting an outwardly expanding radial force to the braided stent body thereby maintaining the lumen of the braided stent body in an opened position, each expansion ring comprising: a plurality of elongate members joined at a coupling and at first and second intersections opposite the coupling; and at least one clip extended from the intersections and operable to secure the frame to the inner and outer surfaces of the lumen;

slidably attaching a plurality of outer strut members of the clip to the inner surface of the lumen, each outer strut member being aligned and extended from the first intersection and joined at an end opposite the first intersection;

slidably attaching a plurality of center strut members of the clip to the outer surface of the lumen, each center strut member being disposed in a gap formed between the outer strut members, the center strut members being aligned and extended from the second intersection; and forming an outer access point at a pore between the outer and center strut members.

14. The method of claim 13, further comprising: attaching the center and outer strut members together at an end opposite the second and first intersections in a pore in communication of the strut members.

15. The method of claim 13, further comprising: forming the shape memory configuration of each expansion ring with a metal alloy tubing structure.

16. The method of claim 13, further comprising: biasing the center and outer strut members together by incorporating a bias element on or about the first and second intersections of the clip.

17. The method of claim 13, further comprising: spacing apart the outer and center strut members a predetermined distance.

* * * * *